(12) United States Patent
Eto

(10) Patent No.: US 11,789,001 B2
(45) Date of Patent: Oct. 17, 2023

(54) INFORMATION PROCESSING APPARATUS, SENSOR OPERATION OPTIMIZATION METHOD, AND PROGRAM

(71) Applicant: NEC Corporation, Tokyo (JP)

(72) Inventor: Riki Eto, Tokyo (JP)

(73) Assignee: NEC CORPORATION, Tokyo (JP)

( * ) Notice: Subject to any disclaimer, the term of this patent is extended or adjusted under 35 U.S.C. 154(b) by 396 days.

(21) Appl. No.: 17/280,439

(22) PCT Filed: Sep. 28, 2018

(86) PCT No.: PCT/JP2018/036505
§ 371 (c)(1),
(2) Date: Mar. 26, 2021

(87) PCT Pub. No.: WO2020/065991
PCT Pub. Date: Apr. 2, 2020

(65) Prior Publication Data
US 2022/0003732 A1      Jan. 6, 2022

(51) Int. Cl.
*G01N 33/00* (2006.01)
(52) U.S. Cl.
CPC ..... *G01N 33/0062* (2013.01); *G01N 33/0036* (2013.01); *G01N 2033/0068* (2013.01)
(58) Field of Classification Search
CPC .......... G01N 33/0036; G01N 33/0062; G01N 2033/68
See application file for complete search history.

(56) References Cited

U.S. PATENT DOCUMENTS

| | | | | |
|---|---|---|---|---|
| 11,668,677 B2 * | 6/2023 | Mlcak | ............... | G01N 29/4454 436/178 |
| 2018/0328767 A1 * | 11/2018 | Adachi | ..................... | G01D 1/18 |
| 2019/0317066 A1 | 10/2019 | Imamura et al. | | |

FOREIGN PATENT DOCUMENTS

| | | | | | |
|---|---|---|---|---|---|
| CN | 108537336 A | * | 9/2018 | ........ | G01N 33/0062 |
| JP | H04-238243 A | | 8/1992 | | |
| JP | H06-102217 A | | 4/1994 | | |
| JP | H11-142313 A | | 5/1999 | | |
| JP | H11142313 A | * | 11/1999 | ............. | B64D 13/06 |
| JP | 2000-155107 A | | 6/2000 | | |
| JP | 2001-175970 A | | 6/2001 | | |
| JP | 2018-087722 A | | 6/2018 | | |
| WO | 2016/052049 A1 | | 4/2016 | | |

OTHER PUBLICATIONS

Machine Translation of CN 108537336 (Year: 2018).*
Machine Translation of JP H11142313 A (Year: 1999).*
International Search Report for PCT Application No. PCT/JP2018/036505, dated Jan. 8, 2019.

* cited by examiner

*Primary Examiner* — Nathaniel J Kolb
(74) *Attorney, Agent, or Firm* — Sughrue Mion, PLLC

(57) ABSTRACT

An information processing apparatus (20) includes a sensor output data acquisition unit (210), a prediction equation generation unit (220), and an operation setting unit (230). The sensor output data acquisition unit (210) acquires sensor output data for each sampling length of an odor sensor with respect to a target gas. The prediction equation generation unit (220) generates, by using the sensor output data for each sampling length, a prediction equation for making a prediction for an odor component of the target gas. The operation setting unit (230) determines, by using the prediction equation, a sampling length for operating the odor sensor.

13 Claims, 6 Drawing Sheets

INFORMATION PROCESSING APPARATUS, SENSOR OPERATION OPTIMIZATION METHOD, AND PROGRAM

This application is a National Stage Entry of PCT/JP2018/036505 filed on Sep. 28, 2018, the contents of all of which are incorporated herein by reference, in their entirety.

TECHNICAL FIELD

The present invention relates to an information processing apparatus, a sensor operation optimization method, and a program.

BACKGROUND ART

A technique for acquiring, by measuring a gas by using a sensor, information relating to the gas has been developed. PTL 1 described below, for example, discloses a technique for identifying an unknown sample by using a transfer function determined based on output of a chemical sensor with respect to input of the unknown sample. Specifically, a technique for 1) providing input in which an amount of an unknown sample changes over time to a chemical sensor, 2) measuring a response changing over time from the chemical sensor, 3) determining, based on the input and the response, a transfer function of the unknown sample, and 4) identifying, based on the determined transfer function, the unknown sample has been disclosed.

CITATION LIST

Patent Literature

[PTL 1] Japanese Patent Application Publication No. 2018-87722

SUMMARY OF INVENTION

Technical Problem

A technique for optimizing, in a chemical sensor (being what is called an odor sensor) that senses an unknown sample (gas), an operation of the sensor in order to increase sensing accuracy for a target odor component is desired.

The present invention has been made in view of the problem described above. One object of the present invention is to provide, in order to increase sensing accuracy for an odor component which is a sensing target of an odor sensor, a technique for optimizing an operation of the sensor.

Solution to Problem

An information processing apparatus according to the present invention includes:

a sensor output data acquisition unit that acquires sensor output data for each sampling length of an odor sensor with respect to a target gas;

a prediction equation generation unit that generates, by using the sensor output data for each sampling length, a prediction equation for making a prediction for an odor component of the target gas; and an operation setting unit that determines, by using the prediction equation, a sampling length for operating the odor sensor.

A sensor operation optimization method executed by a computer according to the present invention includes:

acquiring sensor output data for each sampling length of an odor sensor with respect to a target gas;

generating, by using the sensor output data for each sampling length, a prediction equation for making a prediction for an odor component of the target gas; and determining, by using the prediction equation, a sampling length for operating the odor sensor.

A program according to the present invention causes a computer to execute the above-described sensor operation optimization method.

Advantageous Effects of Invention

According to the present invention, in order to increase sensing accuracy for an odor component which is a sensing target of an odor sensor, an operation of the sensor can be optimized.

BRIEF DESCRIPTION OF DRAWINGS

The above-described object, other objects, features, and advantageous effects will become more apparent from preferred example embodiments described below and the following accompanying drawings.

EXAMPLE EMBODIMENT

Hereinafter, example embodiments according to the present invention are described by using the drawings. Note that, in all the drawings, a similar component is assigned with a similar reference sign and description thereof is omitted, as appropriate.

Note that, in the following description, unless otherwise specially described, each component of each apparatus does not indicate a configuration of a hardware unit but indicates a block of a function unit. Each component of each apparatus is achieved by any combination of hardware and software mainly including a CPU of any computer, a memory, a program achieving a component of the present figure loaded on the memory, a storage medium such as a hard disk storing the program, and a network connection interface. As an achieving method therefor and an apparatus, there are various modified examples.

First Example Embodiment

<Overview>

Figure 1:
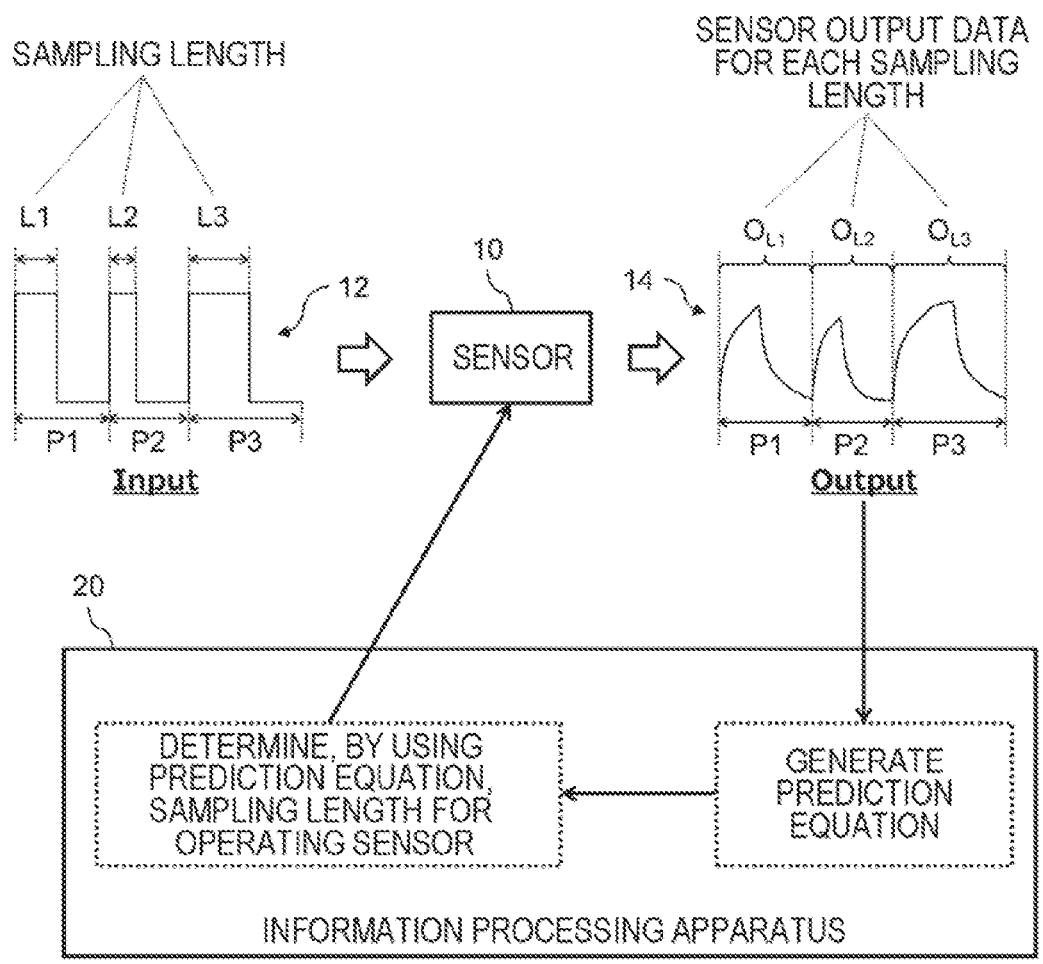
FIG. 1 is a diagram illustrating an overview of an information processing apparatus 20 according to a first example embodiment.

First, by using FIG. 1, an overview of an information processing apparatus 20 according to a first example embodiment is described. FIG. 1 is a diagram illustrating an overview of the information processing apparatus 20 according to the first example embodiment. The information processing apparatus 20 optimizes a sampling length of a sensor 10 for detecting a specific odor component.

Herein, a sensor 10 illustrated in FIG. 1 is a so-called odor sensor. An operation of the sensor 10 (an odor sensor) is configured by repeating sampling and a purge. The "sampling" indicates an operation (e.g., blowing a target gas including an odor component on the sensor 10) of exposing the sensor 10 to a target gas including an odor component, and the "purge" indicates an operation (e.g., exposing the sensor 10 to a purge gas) of eliminating a target gas from the sensor 10. Further, a "sampling length" indicates a length of a period for executing the above-described sampling operation, and a "purge length" indicates a length of a period for executing the above-described purge operation.

In an example in FIG. 1, a reference sign 12 and a reference sign 14 indicate an input signal provided to the sensor 10 and an output signal of the sensor 10 with respect to the input signal, respectively.

In an input signal 12 provided to the sensor 10, a rise period of the signal indicates a period for a sampling operation, and a fall period of the signal indicates a period for a purge operation. In other words, in FIG. 1, L1, L2, and L3 each indicate the sampling length. As illustrated, the sampling lengths L1, L2, and L3 are set to be lengths different from each other. The input signal 12 of the sensor 10 is not specifically limited as long as the input signal has a waveform in which sampling lengths are different from each other in a plurality of periods. Note that, according to the present example embodiment, a purge period has a fixed length. A purge period is set to have a length sufficient for releasing, from the sensor 10, all odor components (molecules) adhering to the sensor 10.

Further, in an output signal 14 of a sensor, $O_{L1}$, $O_{L2}$, and $O_{L3}$ indicate sensor output data (sensor output data for each sampling length) relevant to input of the sampling length L1 in a period P1, input of the sampling length L2 in a period P2, and input of the sampling length L3 in a period P3, respectively.

As illustrated in the figure, the information processing apparatus 20 first acquires the sensor output data ($O_{L1}$, $O_{L2}$, and $O_{L3}$) for each sampling length. The information processing apparatus 20 executes machine learning using the sensor output data for each sampling length and generates a prediction equation. The prediction equation is an equation for making, by using a feature value based on output of the sensor 10, a prediction (e.g., inclusion determination of an odor component) for an odor component of a target gas. The information processing apparatus 20 determines, by using the prediction equation, a sampling length for operating the sensor 10. Specifically, the information processing apparatus 20 determines, by using the generated prediction equation, "what portion of the feature value based on the output of the sensor 10 contributes to a prediction for the odor component of the target gas". The information processing apparatus 20 determines, as a sampling length for operating the sensor 10, a sampling length suitable for acquiring output of the sensor 10 in such a way as to include the feature value contributing to a prediction for the odor component of the target gas.

Function Configuration Example of Information Processing Apparatus 20

Figure 2:
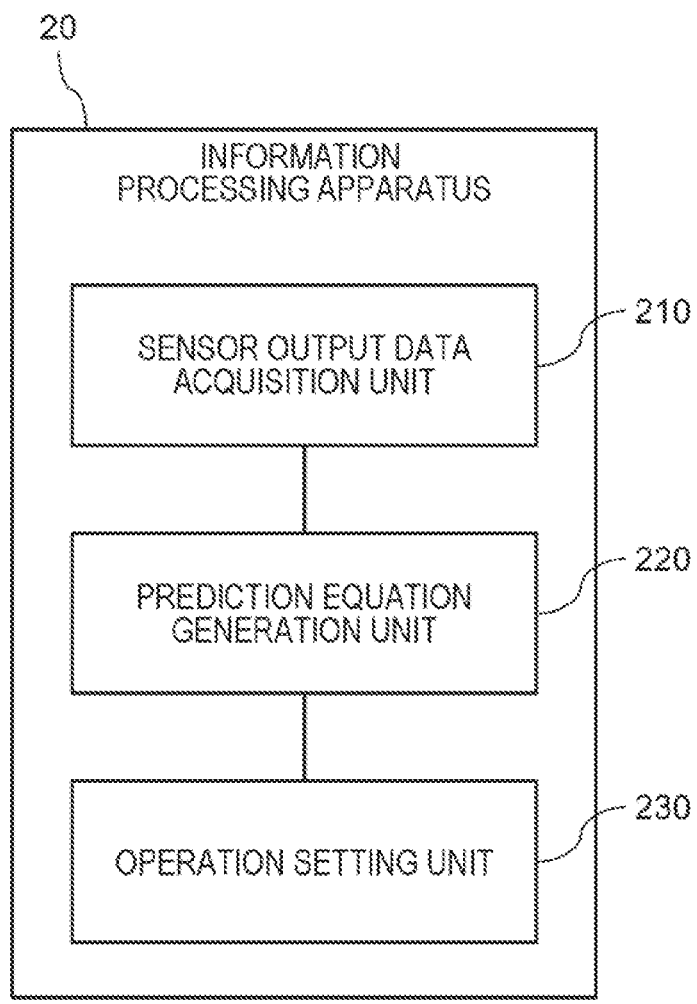
FIG. 2 is a diagram illustrating a function configuration of the information processing apparatus 20 according to the first example embodiment.

FIG. 2 is a diagram illustrating a function configuration of the information processing apparatus 20 according to the first example embodiment. As illustrated in FIG. 2, the information processing apparatus 20 according to the present example embodiment includes a sensor output data acquisition unit 210, a prediction equation generation unit 220, and an operation setting unit 230.

The sensor output data acquisition unit 210 acquires sensor output data (e.g., $O_{L1}$, $O_{L2}$, and $O_{L3}$ in FIG. 1) for each sampling length of an odor sensor with respect to a target gas. The prediction equation generation unit 220 executes machine learning by using the sensor output data for each sampling length, and generates a prediction equation relating to a prediction for an odor component of the target gas. The operation setting unit 230 determines, by using the generated prediction equation, a sampling length for operating the odor sensor.

<Hardware Configuration>

Figure 3:
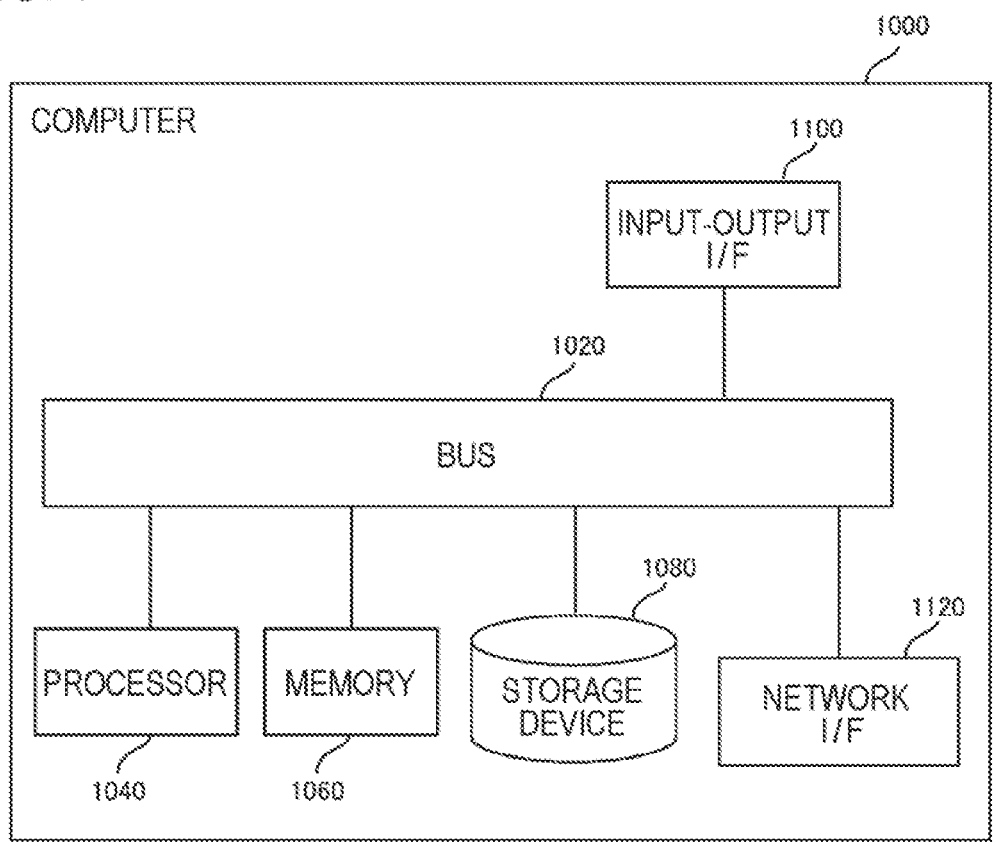
FIG. 3 is a diagram illustrating a computer 1000 for achieving the information processing apparatus 20.

FIG. 3 is a diagram illustrating a computer 1000 for achieving the information processing apparatus 20. The computer 1000 is any computer. The computer 1000 is, for example, a stationary computer such as a personal computer (PC) and a server machine. In addition thereto, the computer 1000 is, for example, a portable computer such as a smartphone and a tablet terminal. The computer 1000 may be a dedicated computer designed for achieving the information processing apparatus 2000 or may be a general-purpose computer.

The computer 1000 includes a bus 1020, a processor 1040, a memory 1060, a storage device 1080, an input-output interface 1100, and a network interface 1120. The bus 1020 is a data transmission path through which the processor 1040, the memory 1060, the storage device 1080, the input-output interface 1100, and the network interface 1120 transmit/receive data to/from each other. However, a method of mutually connecting the processor 1040 and the like is not limited to bus connection.

The processor 1040 includes various types of processors such as a central processing unit (CPU), a graphics processing unit (GPU), and a field-programmable gate array (FPGA). The memory 1060 is a main storage apparatus achieved by using a random access memory (RAM) or the like. The storage device 1080 is an auxiliary storage apparatus achieved by using a hard disk, a solid state drive (SSD), a memory card, a read only memory (ROM), or the like.

The input-output interface 1100 is an interface for connecting the computer 1000 and an input-output device. The input-output interface 1100 is connected to, for example, an input apparatus such as a keyboard and an output apparatus such as a display apparatus. In addition thereto, the input-output interface 1100 is connected to, for example, the sensor 10. However, it is not always necessary for the sensor 10 to be directly connected to the computer 1000. For example, the sensor 10 may cause a storage apparatus shared with the computer 1000 to store output data (sensor output data for each sampling length).

The network interface 1120 is an interface for connecting the computer 1000 to a communication network. The communication network is, for example, a local area network (LAN) and a wide area network (WAN). A method of connecting the network interface 1120 to a communication network may be wireless connection or may be wired connection.

The storage device 1080 stores a program module for achieving each of function-configuring units (the sensor output data acquisition unit 210, the prediction equation generation unit 220, the operation setting unit 230, and the like) of the information processing apparatus 20. The processor 1040 reads each of the program modules onto the memory 1060, executes the read program module, and thereby achieves a function relevant to each of the program modules.

<Flow of Processing>

Figure 4:
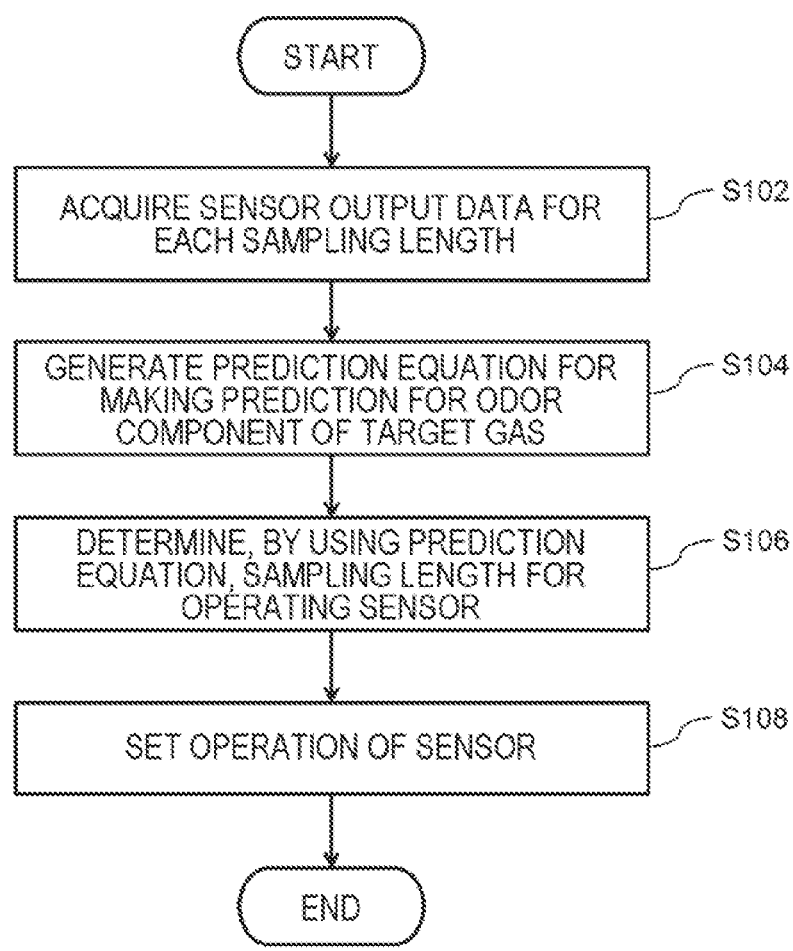
FIG. 4 is a flowchart illustrating a flow of processing executed by the information processing apparatus 20 according to the first example embodiment.

FIG. 4 is a flowchart illustrating a flow of processing executed by the information processing apparatus 20 according to the first example embodiment.

First, the sensor output data acquisition unit 210 acquires sensor output data for each sampling length (S102). As one example, the sensor output data acquisition unit 210 provides a plurality of inputs in which sampling lengths are randomized to the sensor 10 connected via the input-output interface 1100, and as a result, acquires, data (sensor output data) output from the sensor 10. As another example, it may be possible that sensor output data for each sampling length are previously stored in a storage area of the storage device 1080 or the like and the sensor output data acquisition unit 210 reads the sensor output data stored in the storage area.

Next, the prediction equation generation unit 220 generates, by using the sensor output data for each sampling length acquired by the sensor output data acquisition unit 210, a prediction equation for making a prediction for an odor component of a target gas (S104). For example, the prediction equation generation unit 220 converts, by executing Fourier transform or the like, the pieces of sensor output data (e.g., $O_{L1}$, $O_{L2}$, and $O_{L3}$ in FIG. 1) for each sampling length to pieces of feature data of a frequency region, executes machine learning by using the pieces of feature data, and generates the prediction equation. Specifically, the prediction equation generation unit 220 executes, by using the feature data acquired from the sensor output data for each sampling length, sparse learning such as least absolute shrinkage and selection operator (LASSO), and determines a prediction model (prediction equation) represented by "(a prediction result: an objective variable)=f(feature data of a frequency region: an explanatory variable)". When sparse learning is executed, one or more frequency components (feature values) contributing to a prediction for an odor component of a target gas are selected. The prediction equation generation unit 220 generates a prediction equation in which a weight coefficient for a frequency component other than the one or more frequency components being selected based on sparse learning is 0.

A prediction equation is, for example, a linear sum of feature values and is represented by z=WX+b. Herein, X is a feature value vector based on output of the sensor 10, W is a weight coefficient vector indicating a weight coefficient relevant to each element (feature value) of the feature value vector X, and b is a constant. An acquired z indicates a prediction result. A prediction equation may be used for determination or may be used for a regressive prediction. For example, in a prediction equation used for determining a presence/absence of a certain odor component, when z is equal to or more than a predetermined reference, it is possible to determine that an odor component of a detection target is included in a gas to be measured, and when z is less than the reference, it is possible to determine that the odor component of the detection target is not included in the gas to be measured. Examples of a regressive prediction include a prediction of production quality based on an odor of a product such as a beverage, a prediction of a state in a body based on measurement of exhaled breath, and the like.

Next, the operation setting unit 230 determines, by using the prediction equation generated by the prediction equation generation unit 220, a sampling length for operating the sensor 10 (S106). Specifically, the operation setting unit 230 determines, by using a weight coefficient for each frequency component in the prediction equation, the sampling length for operating the sensor 10.

First, the operation setting unit 230 determines, based on a weight coefficient for each frequency component in the prediction equation, a frequency component having a value of a weight coefficient other than 0. The operation setting unit 230 executes inverse Fourier transform for the determined frequency component. As a result, an ideal first waveform is acquired as output (a signal of a time region) of the sensor 10 used for a prediction for a target odor component. The operation setting unit 230 converts, by using an inverse transfer function of the sensor 10, the first waveform to an ideal second waveform as input of the sensor 10. Herein, the inverse transfer function of the sensor 10 can be derived, for example, based on a transfer function of the sensor 10. Note that, the operation setting unit 230 can compute, based on a combination of an input signal and an output signal of the sensor 10, the transfer function of the sensor 10. The operation setting unit 230 can determine, from the second waveform acquired in this manner, a sampling length optimum for an operation of the sensor 10. The operation setting unit 230 can determine, as a sampling length for operating the sensor 10, for example, a length of a rise period of a signal in the second waveform. Note that, when a plurality of frequency components are selected as a result of executing sparse learning, the operation setting unit 230 can acquire, as a result of inverse Fourier transform, the second waveform including a plurality of sampling lengths. The operation setting unit 230 can determine, as a sampling length for operating the sensor 10, each of a plurality of sampling lengths based on the second waveform. However, specific operations described here each represent merely one example, and an operation of the operation setting unit 230 is not limited to the examples.

The operation setting unit 230 sets, based on the sampling length determined by the processing of S106 and a purge length being a fixed value, the operation of the sensor 10 (a switching cycle of sampling/purge of the sensor 10) (S108). Note that, information relating to a purge length being a fixed value is previously stored, for example, in a storage area of the memory 1060, the storage device 1080, or the like, and the operation setting unit 230 can acquire, from the storage area, the information relating to the purge length.

Advantageous Effect

As described above, according to the present example embodiment, first, by using sensor output data for each sampling length acquired from an odor sensor as a response to each of a plurality of inputs different in sampling length, a prediction equation for making a prediction for the odor component is generated. By using the generated prediction equation, a feature value (e.g., a frequency component) contributing to a prediction for the odor component is determined. A sampling length suitable for acquiring output of the sensor 10 including the determined feature value is determined as a "sampling length for operating an odor sensor". In other words, according to the present example embodiment, an operation of an odor sensor can be optimized in such a way that a feature value contributing to a prediction for an odor component of a target gas is included in output of the sensor 10. Thereby, an advantageous effect of reducing a possibility of making a false prediction for a target odor component is expectable.

Specific Use Example

A method of optimizing the above-described operation of the sensor 10 can be executed, for example, in a site where the sensor 10 is provided. Specifically, a gas (sample gas) including an odor component of a sensing target is carried to a site where the sensor 10 is provided, and thereby the operation of the sensor 10 can be optimized based on the following procedure.

1) Sensor output data for each sampling length acquired by exposing, based on various lengths, the sensor 10 to the sample gas are input to the information processing apparatus 20.

2) The information processing apparatus 20 generates, by using the sensor output data for each sampling length acquired in above 1), a prediction equation for making a prediction for the odor component of the sensing target.

3) The information processing apparatus 20 determines, by using the prediction equation generated in above 2), a sampling length for operating the sensor 10, and sets the determined sampling length to the sensor 10.

In this manner, according to the present, example embodiment, in a site where the sensor 10 is provided, the operation of the sensor 10 can be simply tuned.

Note that, when a plurality of types of odors are a sensing target such as when, for example, both of a burning odor of rubber and a melting odor of plastic are sensed, the information processing apparatus 20 executes the above-described processing for each odor of the sensing target, and determines a sampling length optimum for each odor of the sensing target. In this case, the information processing apparatus 20 optimizes, by using the sampling length determined for each odor of the sensing target, the operation of the sensor 10. Specifically, when there are two types of odors in a sensing target, the information processing apparatus 20 determines, with respect to first and second odors, a first sampling length and a second sampling length, respectively. The information processing apparatus 20 sets, as an operation of one cycle of the sensor 10, for example, "a sampling operation in a first sampling length→a purge operation of a fixed length→a sampling operation in a second length→a purge operation of a fixed length". By doing so, even when a plurality of types of odors are a detection target, an operation of a sensor 10 can be optimized in such a way as to be able to accurately sense each odor.

Second Example Embodiment

Output of a sensor 10 may vary depending on not only a component of a target gas but also a measurement environment (measurement condition) for the component. As a specific example, there is a case where when a spring exists as one component of the sensor 10, a spring coefficient varies depending on temperature, humidity, and the like, and then outputs for the same input may differ. Due to this reason, a sampling length suitable for acquiring the output of the sensor 10 including a feature of an odor component may differ with respect to each measurement environment. The information processing apparatus 20 according to the present example embodiment includes a configuration for solving the problem.

Function Configuration Example

The information processing apparatus 20 according to the present example embodiment is the same as the information processing apparatus 20 according to the first example embodiment, except a point described below. According to the present example embodiment, a prediction equation generation unit 220 classifies, based on a measurement environment of the sensor 10, sensor output data for each sampling length, and generates, by using the sensor output data for each measurement environment, a prediction equation for each measurement environment of the sensor 10. A method of generating the prediction equation is similar to the first example embodiment. Further, an operation setting unit 230 determines, with respect to each measurement environment, a sampling length for operating the sensor 10 by using the prediction equation generated for each measurement environment of the sensor 10. A method of determining a sampling length is similar to the first example embodiment.

Specific examples of the above-described measurement environment include, but not specifically limited to, for example, temperature, humidity, an air pressure, a type of a contaminating gas, a type of a purge gas, a distance between a sensing target object and a sensor, an object existing around the sensor, and the like. Temperature, humidity, and an air pressure are temperature, humidity, and an air pressure around a sensor 10, specifically, temperature, humidity, and an air pressure of an atmosphere surrounding a functional unit of the sensor 10. A type of the contaminating gas is a type of a gas supplied to the sensor 10 together with a target odor component in an operation (sampling) of exposing the sensor 10 to a target gas. Specifically, a type of the contaminating gas includes an inert gas such as nitrogen, air, and the like. A type of the purge gas is a gas supplied to the sensor 10 in an operation (purge) of eliminating a gas to be measured from the sensor 10. Specifically, the purge gas includes an inert gas such as nitrogen, air, and the like. The distance between the target object and the sensor 10 is a distance between the target object and the sensor 10 in which the sensor 10 is disposed around a specific target object and detection is performed. The object existing around the sensor 10 is a type of a target object in which the sensor 10 is disposed around a specific target object and detection is performed.

Advantageous Effect

As described above, according to the present example embodiment, by using sensor output data for each measurement environment, a prediction equation is generated for each measurement environment, and by using the prediction equation for each measurement environment, a sampling length is determined for each measurement environment. Thereby, an operation of the sensor 10 can be optimized according to a measurement environment.

Third Example Embodiment

An information processing apparatus 20 according to the present example embodiment includes a configuration similar to the above-described example embodiments except a point described below, <Overview>

Figure 5:
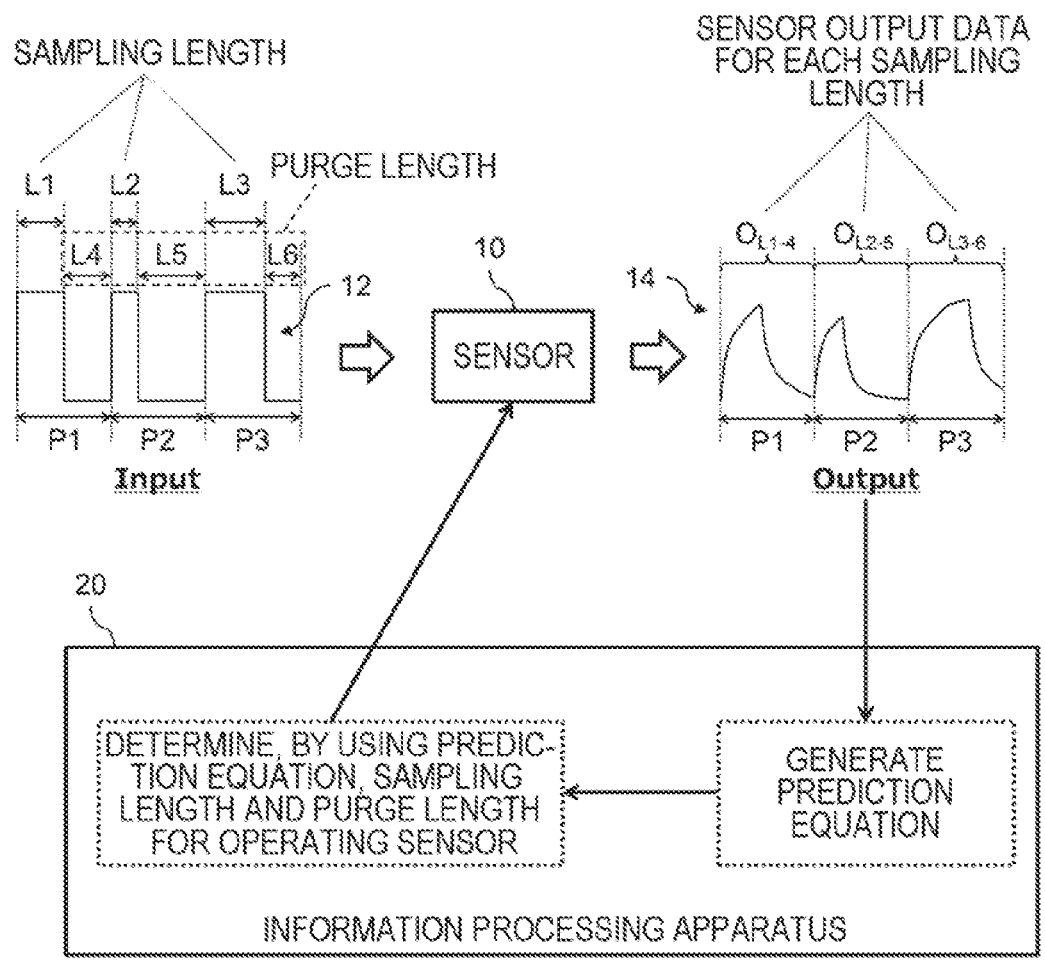
FIG. 5 is a diagram illustrating an overview of the information processing apparatus 20 according to the third example embodiment.

By using FIG. 5, an overview of the information processing apparatus 20 according to a third example embodiment is described. FIG. 5 is a diagram illustrating an overview of the information processing apparatus 20 according to the third example embodiment. The example in FIG. 5 and the example in FIG. 1 are different in a waveform of an input signal 12. While in the example in FIG. 1, a purge length (a fall period of a signal) of the input signal 12 is fixed, in the example in FIG. 5, the purge length is variable. Specifically, L1, L2, and L3 in FIG. 5 each indicate a sampling length. As illustrated, sampling lengths L1, L2, and L3 are set to be different in length from each other. Further, L4, L5, and L6 each indicate a purge length. As illustrated, purge lengths L4, L5, and L6 are set to be different in length from each other. The input signal 12 as illustrated in FIG. 5 is generated, for example, by using a logic circuit generating an M-sequence signal.

Further, in an output signal 14 of a sensor, $O_{L1-4}$, $O_{L2-5}$, and $O_{L3-6}$ each indicate sensor output data (sensor output data for each combination of a sampling length and a purge length) relevant to input of a combination of the sampling length L1 and the purge length L4 in a period P1, input of a combination of the sampling length L2 and the purge length L5 in a period P2, and input of a combination of the sampling length L3 and the purge length L6 in a period P3.

As illustrated in the figure, the information processing apparatus 20 first acquires the sensor output data ($O_{L1-4}$, $O_{L2-5}$, and $O_{L3-6}$) for each combination of the sampling length and the purge length. The information processing apparatus 20 executes machine learning using the sensor output data for each sampling length and generates a prediction equation. The prediction equation is an equation for making, by using a feature value based on output of the sensor 10, a prediction (e.g., inclusion determination of an odor component) for an odor component of a target gas. The information processing apparatus 20 determines, by using the prediction equation, a sampling length for operating the sensor 10. Specifically, the information processing apparatus 20 determines, by using the generated predication equation, "what portion of the feature value based on the output of the sensor 10 contributes to a prediction for the odor component of the target gas". The information processing apparatus 20 determines, as a sampling length and a purge length for operating the sensor 10, a sampling length and a purge length suitable for acquiring output of the sensor 10 in such a way as to include the feature value contributing to a prediction for the odor component of the target gas.

Function Configuration Example

The information processing apparatus 20 according to the present example embodiment includes a configuration similar to the configuration (e.g., FIG. 1) illustrated according to the first example embodiment. According to the present example embodiment, a sensor output data acquisition unit 210 acquires sensor output data for each combination of a sampling length and a purge length of a sensor 10 (an odor sensor). Further, a prediction equation generation unit 220 executes machine learning by using the sensor output data for each combination of the sampling length and the purge length, and generates a prediction equation relating to a prediction for an odor component of a target gas. An operation setting unit 230 determines, by using the generated prediction equation, a sampling length and a purge length for operating the odor sensor.

<Flow of Processing>

Figure 6:
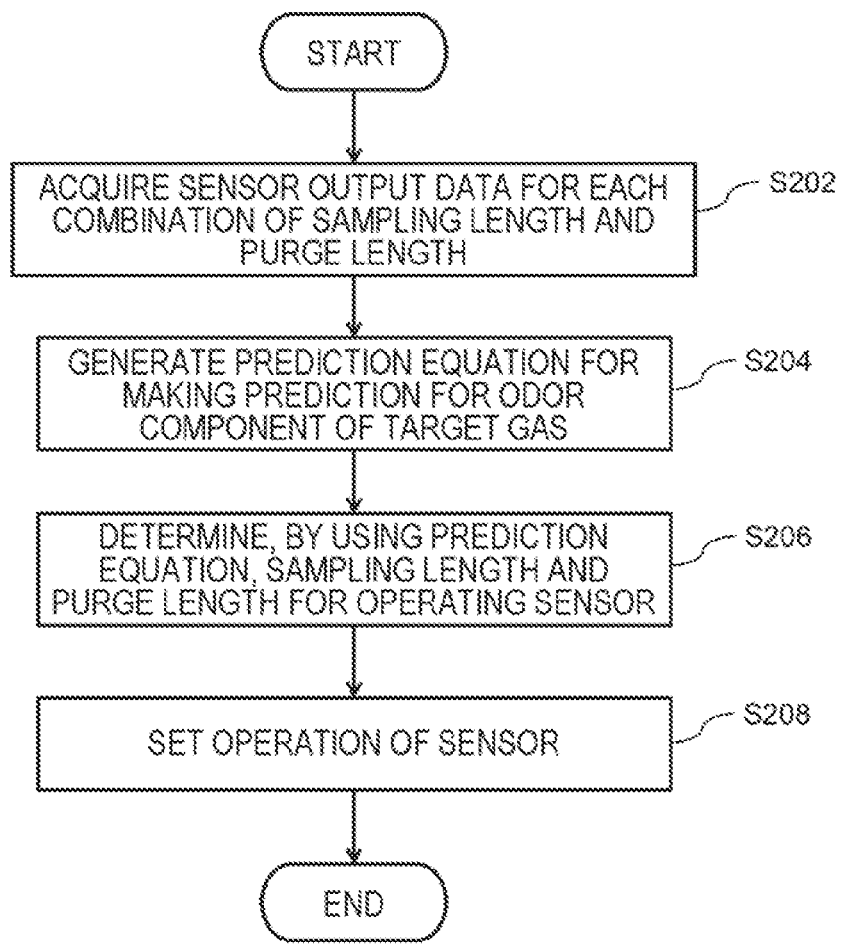
FIG. 6 is a flowchart illustrating a flow of processing executed by an information processing apparatus 20 according to a third example embodiment.

FIG. 6 is a flowchart illustrating a flow of processing executed by then information processing apparatus 20 according to the third example embodiment.

First, the sensor output data acquisition unit 210 acquires sensor output data for each combination of a sampling length and a purge length (S202). As one example, the sensor output data acquisition unit 210 provides a plurality of inputs in which sampling lengths and purge lengths are randomized to the sensor 10 connected via an input-output interface 1100, and as a result, acquires data (sensor output data) output from the sensor 10. As another example, it may be possible that sensor output data for each combination of the sampling length and the purge length are previously stored in a storage area of a storage device 1080 or the like and the sensor output data acquisition unit 210 reads the sensor output data stored in the storage area.

Next, the prediction equation generation unit 220 generates, by using the sensor output data for each combination of the sampling length and the purge length acquired by the sensor output data acquisition unit 210, a prediction equation for making a prediction for an odor component of a target gas (S204). The prediction equation generation unit 220 selects, similarly to the first example embodiment, one or more frequency components contributing to a prediction for an odor component of a target gas, based on sparse learning, and generates a prediction equation in which a weight coefficient for a frequency component other than the one or more frequency components is 0.

Next, the operation setting unit 230 determines, by using the prediction equation generated by the prediction equation generation unit 220, a sampling length and a purge length for operating the sensor 10 (S206). Specifically, the operation setting unit 230 determines, by using a weight coefficient for each frequency component in the prediction equation, the sampling length and the purge length for operating the sensor 10.

First, the operation setting unit 230 determines, based on a weight coefficient for each frequency component in the prediction equation, a frequency component having a value of a weight coefficient other than 0. The operation setting unit 230 executes inverse Fourier transform for the determined frequency component. As a result, an ideal first waveform is acquired as output (a signal of a time region) of the sensor 10 used for a prediction for a target odor component. The operation setting unit 230 converts, by using an inverse transfer function of the sensor 10, the first waveform to an ideal second waveform as input of the sensor 10. Herein, the inverse transfer function of the sensor 10 can be derived, for example, based on a transfer function of the sensor 10. Note that, the operation setting unit 230 can compute, based on a combination of an input signal and an output signal of the sensor 10, the transfer function of the sensor 10. The operation setting unit 230 can determine, from the second waveform acquired in this manner, a sampling length and a purge length optimum for an operation of the sensor 10. The operation setting unit 230 can determine, as a sampling length for operating the sensor 10, a length of a rise period of a signal in the second waveform. Further, the operation setting unit 230 can determine, as a purge length for operating the sensor 10, a length of a fall period of a signal in the second waveform. Note that, when a plurality of frequency components are selected as a result of executing sparse learning, the operation setting unit 230 can acquire, as a result of inverse Fourier transform, the second waveform including a plurality of sampling lengths and a plurality of purge lengths. The operation setting unit 230 can determine, as a sampling length for operating the sensor 10, each of a plurality of sampling lengths based on the second waveform. Further, the operation setting unit 230 can determine, as a purge length for operating the sensor 10, a plurality of purge lengths based on the second waveform. However, specific operations described here each represent merely one example, and an operation of the operation setting unit 230 is not limited to the examples.

The operation setting unit 230 sets, based on the sampling length and the purge length (a switching cycle of sampling/purge of the sensor 10) determined by processing of S206, the operation of the sensor 10 (S208).

As described above, according to the present example embodiment, based on a cycle determined as a cycle optimum for an operation of the sensor 10, a sampling length and a purge length for operating the sensor 10 are determined. Based on the determined sampling length and purge length, an operation of the sensor 10 is tuned. Not only a sampling length but also a purge length is adjusted, and thereby an operation of an odor sensor can be accurately optimized.

While the example embodiments of the present invention have been described with reference to the drawings, the example embodiments are only exemplification of the present invention, and various configurations other than the above-described example embodiments can also be employed.

Further, in a plurality of flowcharts used in the above-described description, a plurality of steps (processing) are described in order, but an execution order of steps to be executed in each example embodiment is not limited to the described order. According to the example embodiments, an order of illustrated steps can be modified within an extent that there is no harm in context. Further, the above-described example embodiments can be combined within an extent that there is no conflict in content.

What is claimed is:

1. An information processing apparatus comprising:
   a sensor output data acquisition unit that acquires sensor output data for each sampling length of an odor sensor with respect to a target gas;
   a prediction equation generation unit that generates, by using the sensor output data for each sampling length, a prediction equation for making a prediction for an odor component of the target gas; and
   an operation setting unit that determines, by using the prediction equation, a sampling length for operating the odor sensor.

2. The information processing apparatus according to claim 1, wherein
   the prediction equation generation unit
      converts each piece of the sensor output data for each sampling length to feature data of a frequency region, and
      generates the prediction equation by using the feature data of the frequency region.

3. The information processing apparatus according to claim 2, wherein
   the prediction equation includes a weight coefficient for each frequency, and
   the operation setting unit determines, by using the weight coefficient for each frequency, the sampling length for operating the odor sensor.

4. The information processing apparatus according to claim 1, wherein
   the prediction equation generation unit generates, by using the sensor output data for each measurement environment classified based on a measurement environment of the odor sensor, the prediction equation for each measurement environment of the odor sensor, and
   the operation setting unit determines, by using a weight of the prediction equation generated for each measurement environment of the odor sensor, the sampling length for each measurement environment.

5. The information processing apparatus according to claim 4, wherein
   the measurement environment includes at least any one of temperature, humidity, an air pressure, a type of a contaminating gas, a type of a purge gas, a distance between a target object and the odor sensor, and an object existing around the odor sensor.

6. The information processing apparatus according to claim 1, wherein
   the sensor output data acquisition unit acquires sensor output data for each combination of a sampling length and a purge length of the odor sensor,
   the prediction equation generation unit generates the prediction equation, by using the sensor output data for each combination, and
   the operation setting unit determines, by using the prediction equation, the sampling length and the purge length.

7. A sensor operation optimization method executed by a computer, the method comprising:
   acquiring sensor output data for each sampling length of an odor sensor with respect to a target gas;
   generating, by using the sensor output data for each sampling length, a prediction equation for making a prediction for an odor component of the target gas; and
   determining, by using the prediction equation, a sampling length for operating the odor sensor.

8. The sensor operation optimization method executed by the computer according to claim 7, the method further comprising:
   converting each piece of the sensor output data for each sampling length to feature data of a frequency region; and
   generating the prediction equation by using the feature data of the frequency region.

9. The sensor operation optimization method executed by the computer according to claim 8, wherein
   the prediction equation includes a weight coefficient for each frequency region; and
   the method further comprising:
      determining, by using the weight coefficient for each frequency, the sampling length for operating the odor sensor.

10. The sensor operation optimization method executed by the computer according to claim 7, the method further comprising:
    generating, by using the sensor output data for each measurement environment classified based on a measurement environment of the odor sensor, the prediction equation for each measurement environment of the odor sensor; and
    determining, by using a weight of the prediction equation generated for each measurement environment of the odor sensor, the sampling length for each measurement environment.

11. The sensor operation optimization method according to claim 10, wherein the measurement environment includes at least any one of temperature, humidity, an air pressure, a type of a contaminating gas, a type of a purge gas, a distance between a target object and the odor sensor, and an object existing around the odor sensor.

12. The sensor operation optimization method executed by the computer according to claim 7, the method further comprising:
    acquiring sensor output data for each combination of a sampling length and a purge length of the odor sensor;
    generating the prediction equation, by using the sensor output data for each combination; and
    determining, by using the prediction equation, the sampling length and the purge length.

13. A non-transitory computer readable medium storing a program causing a computer to execute a sensor operation optimization method, the method comprising:

acquiring sensor output data for each sampling length of an odor sensor with respect to a target gas;
generating, by using the sensor output data for each sampling length, a prediction equation for making a prediction for an odor component of the target gas; and
determining, by using the prediction equation, a sampling length for operating the odor sensor.

* * * * *